United States Patent
Zecchino et al.

(10) Patent No.: US 10,849,844 B2
(45) Date of Patent: Dec. 1, 2020

(54) FORMULATIONS FOR TREATMENT OF SKIN AND METHODS OF MAKING AND USING THE SAME

(71) Applicant: BioMimetic Laboratories Inc., New York, NY (US)

(72) Inventors: Julius R. Zecchino, Closter, NJ (US); Marina Zecchino, New York, NY (US); Konstantinos Lahanas, Paramus, NJ (US)

(73) Assignee: BioMimetic Laboratories Inc., New York, NY (US)

( * ) Notice: Subject to any disclaimer, the term of this patent is extended or adjusted under 35 U.S.C. 154(b) by 0 days.

(21) Appl. No.: 15/573,299

(22) PCT Filed: May 13, 2016

(86) PCT No.: PCT/US2016/032373
§ 371 (c)(1),
(2) Date: Nov. 10, 2017

(87) PCT Pub. No.: WO2016/187012
PCT Pub. Date: Nov. 24, 2016

(65) Prior Publication Data
US 2018/0133140 A1    May 17, 2018

Related U.S. Application Data

(60) Provisional application No. 62/162,412, filed on May 15, 2015.

(51) Int. Cl.
| | |
|---|---|
| A61K 8/81 | (2006.01) |
| A61K 8/49 | (2006.01) |
| A61Q 19/00 | (2006.01) |
| A61Q 19/08 | (2006.01) |
| A61K 8/362 | (2006.01) |
| A61K 8/9789 | (2017.01) |
| A61K 8/36 | (2006.01) |

(52) U.S. Cl.
CPC ............ *A61K 8/8158* (2013.01); *A61K 8/361* (2013.01); *A61K 8/362* (2013.01); *A61K 8/4973* (2013.01); *A61K 8/9789* (2017.08); *A61Q 19/00* (2013.01); *A61Q 19/007* (2013.01); *A61Q 19/08* (2013.01)

(58) Field of Classification Search
None
See application file for complete search history.

(56) References Cited

U.S. PATENT DOCUMENTS

| | | |
|---|---|---|
| 2007/0166267 A1 | 7/2007 | Majewski et al. |
| 2007/0207112 A1 | 9/2007 | Gormley et al. |

OTHER PUBLICATIONS

International Search Report (PCT/ISA/210) issued in PCT Application No. PCT/US2016/032373 dated Aug. 1, 2016 (Two (2) pages).
International Preliminary Report on Patentability (PCT/IB/326 & PCT/IB/373) issued in PCT Application No. PCT/US/2016/032373 dated Nov. 30, 2017 including Written Opinion (PCT/ISA/237) (Seven (7) pages).
Fischer, et al., "Direct and Non-Direct Measurement Techniques for Analysis of Skin Surface Topography," Skin Pharmacology and Applied Skin Physiology, Journal of Pharmacological and Biophysical Research,Technical Review, 1999, 12:1-11 (Thirteen (13) pages).
Farwick, et al., "An ECM-Derived Tetrapeptide to Counterbalance ECM Degeneration," Cosmetics & Toiletries Magazine, Jun. 2009, vol. 124, No. 6, pp. 51-54 (Four (4) pages).
Agache, et al., "Mechanical Properties and Young's Modulus of Human Skin in Vivo," Archives of Dermatological Research, vol. 269, 1980, pp. 221-232 (Twelve (12) pages).
De Rigal, et al., "In Vivo Measurement of the Stratum Corneum Elasticity," Bioengineering and the Skin, The Official Journal of the International Society for Bioengineering and the Skin, Jan. 1985, vol. 1, No. 1, pp. 13-23 (Fifteen (15) pages).
Leveque et al., "Impedance Methods for Studying Skin Moisturization," Journal of the Society of Cosmetic Chemists, Dec. 1983, vol. 34, No. 1, pp. 419-428 (Eleven (11) pages).

*Primary Examiner* — David J Blanchard
*Assistant Examiner* — Sarah J Chickos
(74) *Attorney, Agent, or Firm* — Crowell & Moring LLP

(57) ABSTRACT

The present invention relates to topical formulations designed to improve the delivery of active agents to the skin, thus improving the look and/or feel of skin, as well as methods of making and using such formulations. The present invention is useful for producing healthier, more radiant skin, with reduced dryness, dullness, wrinkles and fine lines, redness and blotchiness of skin, and the like.

12 Claims, No Drawings

FORMULATIONS FOR TREATMENT OF SKIN AND METHODS OF MAKING AND USING THE SAME

CROSS-REFERENCE TO RELATED APPLICATIONS

The present application claims the benefit of pending PCT International Application No. PCT/US2016/032373, filed May 13, 2016, published as WO 2016/187012, which PCT International Application claims the benefit of U.S. Provisional Application No. 62/162,412, filed May 15, 2015, both of which applications are hereby incorporated by reference in their entireties.

FIELD OF THE INVENTION

The present invention relates to topical formulations designed to improve the delivery of active agents to the skin, thus improving the look and/or feel of skin, as well as methods of making and using such formulations. In this way, the present invention is useful for producing healthier, more radiant skin, with reduced dryness, dullness, wrinkles and fine lines, redness and blotchiness of skin, and the like.

BACKGROUND OF THE INVENTION

Skin serves to protect the body from the environment, helps to control body temperature and fluid and electrolyte balance. Environmental assaults to the skin, such as exposure to pollutants, extreme temperatures, UV radiation, other internal and external stressors, and simply time, can significantly impact the way skin ages. Among the most visible signs of aging are changes in the skin. The skin typically becomes drier, develops wrinkles and begins to sag. Dryness of skin is also often associated with redness, itching, and irritation. The cosmetic industry continues to search for unique compounds and formulations to counter the adverse effects of premature skin aging and improve the look and feel of skin.

SUMMARY OF THE INVENTION

Described herein are formulations to counter conditions associated with pre-mature skin aging and dry skin and provide aesthetically pleasing look, feel and finish to the skin. The formulations improve the feel and look (e.g., radiance) of the skin. Use, particularly including repeated use, smooths and reduces the look of fine-lines, wrinkles and/or sagging.

Provided are topical skin formulations designed to improve delivery, including penetration and retention of active agents. It has been unexpectedly discovered that a combination of dimethyl isosorbide, an oleic acid, and InvisaSkin® (which, as used herein, unless otherwise specified, includes InvisaSkin® RB, InvisaSkin® DS, or both in any proportion) provides unexpectedly enhanced beneficial effects as compared with effects of prior proprietary and competitor formulations, which are referred to herein as conventional skin care products. The combination of dimethyl isosorbide, an oleic acid, and InvisaSkin® allows for improved penetration and retention of the chosen active agent as compared with conventional skin care products. Indeed, the look and feel of the skin is improved to an unexpectedly enhanced degree upon use of the present formulations as compared with use of conventional skin care products.

The present formulations provide many positive results, including a reduction in fine lines and wrinkles, an increase in elasticity, flexibility or both, an improvement in skin moisture content, and an increased skin brightness, clarity, uniformity or any thereof. An active agent may also improve the health of skin or reduce pain or swelling of skin.

The present invention provides improved delivery of an active agent to skin, where the dimethyl isosorbide and the oleic acid opens skin pores, facilitating absorption of one or more active agent for moisturizing skin. The present invention, alternatively or additionally, facilitates retention of one or more active agents, as the InvisaSkin® closes skin pores. Thus, the present invention provides formulations comprising a dimethyl isosorbide, an oleic acid, and InvisaSkin®. As noted above, InvisaSkin® includes InvisaSkin® RB, InvisaSkin® DS, or both. Both InvisaSkin® RB and InvisaSkin® DS are proprietary compositions of Grant Industries (Elmwood Park, N.J.).

InvisaSkin® DS may be used herein in place of InvisaSkin® RB, and vice versa, or the two may be mixed in any proportion to achieve a stated weight percent for a formulation of the present invention.

The ingredients of the present formulations are provided herein by weight percentage, unless otherwise specified. For example, the present invention provides formulations comprising about 1-20% dimethyl isosorbide, about 0.1-20% oleic acid, and about 0.5-10% InvisaSkin®. The present invention also includes formulations comprising about 2-10% dimethyl isosorbide, about 0.5-10% oleic acid, and about 1-5% InvisaSkin®. The present invention also includes and provides formulations comprising about 6% dimethyl isosorbide, about 0.5% oleic acid, and about 1.5% InvisaSkin®.

For example, the present invention provides formulations comprising about 1-20% dimethyl isosorbide, about 0.1-20% oleic acid, and about 0.5-10% InvisaSkin® RB. The present invention also includes formulations comprising about 2-10% dimethyl isosorbide, about 0.5-10% oleic acid, and about 1-5% InvisaSkin® RB. The present invention also includes and provides formulations comprising about 6% dimethyl isosorbide, about 0.5% oleic acid, and about 1.5% InvisaSkin® RB. Formulations of the present invention optionally further comprise one or more glycols, which may act as humectants, where a humectant, as used herein, is an ingredient that acts in reducing loss of skin moisture. An exemplary, non-limiting glycol is butylene glycol. Another exemplary, non-limiting glycol is pentylene glycol.

In an embodiment of the present invention, formulations include one or more active agents. An active agent may include one that moisturizes skin, reduces fine lines, wrinkles, and sagging skin, otherwise improves the look, feel, texture, or radiance of skin, or any combination thereof. Additionally or alternatively, an active agent may include a pharmaceutically active agent whose activity is pharmacological such as for example antimicrobial, antihistamine, anti-inflammatory, anti-stress, anti-redness, anti-pigmentation, or analgesic activity. Non-limiting exemplary active agents include antioxidants, vitamins, plant extracts, anti-aging peptides, anti-wrinkle peptides, UV absorbers, and/or NO MOBO BT (BC Research, Elmwood Park, N.J.). Exemplary active agents also include other water soluble compounds that improve the look and feel of skin.

The present invention includes and provides formulations comprising about 1-20% dimethyl isosorbide, about 0.1-1% oleic acid, about 0.5-4% InvisaSkin®, and about 0.5-5% NO MOBO BT. For example, the present invention includes and provides formulations comprising about 1-20% dimethyl isosorbide, about 0.1-1% oleic acid, about 0.5-4% InvisaSkin® RB, and about 0.5-5% NO MOBO BT.

The present invention also includes and provides formulations comprising about 5-90% deionized water, about 0.1-0.5% carbopol ultrez 10 polymer, about 0.5-3% Steareth-21, about 0.5-3% Tween 20, about 0.5-2% diocide, about 0.5-3% sodium hyaluronate 2% aq. sol., about 0.5-4% white birch BT, about 0.5-5% NO MOBO BT, about 1-20% dimethyl isosorbide, 1-10% Algogen 2000, about 0.05-0.3% Caffeine, about 0.5-3% TEGO® COSMO C 100, about 0.5-4% InvisaSkin RB®, about 0.5-3% niacinamide PC, about 0.01-1% Glabridin, about 0.5-3% BEAUTIFEYE™, about 0.5-3% Whey Protein Concentrate 80%, about 8-18% Aurasphere® N, about 5-18% Gransil GCM-5, about 5-15% Gransil EP-9, about 1-5% Gransil 530, about 1-4% Phytolane LS, about 0.1-1% oleic acid, about 0.5-5% Dimethicone 20 CST, about 1-5% KOH 10% aq. sol., about 1-5% Hydrolite-5, about 0.1-2% Simulgel EG, about 2-8% Argireline® NP, about 0.05-2% *Magnolia* Super Extract, about 2-8% XEP-018, about 0.5-3% X-50 0.10% aq. sol., about 2-8% CL-2080, about 1-3% Timiron Super Red, about 0.01-0.08% Red No. 4 in butylene glycol sol. 1%, about 0.1-0.6% fragrance.

The present invention includes and provides methods for improved delivery of an active agent to skin, such method including administering a formulation that comprises dimethyl isosorbide, oleic acid, and InvisaSkin®, where InvisaSkin® is InvisaSkin® RB, InvisaSkin® DS, or both.

The present invention includes and provides methods for improved delivery of an active agent to skin, where the formulation administered includes about 1-20% dimethyl isosorbide, about 0.1-20% oleic acid, and about 0.5-10% InvisaSkin® RB. The present invention also includes and provide methods where the formulation includes about 2-10% dimethyl isosorbide, about 0.5-10% oleic acid, and about 1-5% InvisaSkin® RB, or alternatively the formulation may include about 6% dimethyl isosorbide, about 0.5% oleic acid, and about 1.5% InvisaSkin® RB.

Water, including for example deionized water, may optionally be added to any formulation of the present invention in a weight percent from 5% to 90%.

The present invention also includes and provides methods for improved delivery of an active agent to skin, where the formulation administered further comprises one or more glycols as a humectant, an active agent (e.g., NO MOBO BT), or both. By way of example, the present invention includes and provides a method for improved delivery of an active agent to skin, where the formulation administered includes about 1-20% dimethyl isosorbide, about 0.1-1% oleic acid, about 0.5-4% InvisaSkin®, and about 0.5-5% NO MOBO BT. As a further example, the present invention includes and provides a method for improved delivery of an active agent to skin, where the formulation administered includes about 1-20% dimethyl isosorbide, about 0.1-1% oleic acid, about 0.5-4% InvisaSkin® RB, and about 0.5-5% NO MOBO BT.

The present invention also includes and provides methods for making each of the formulations of the present invention as taught herein for topical administration to the skin.

DETAILED DESCRIPTION OF THE INVENTION

Described herein are topical formulations to counter conditions associated with pre-mature skin aging and dry skin and provide aesthetically pleasing look, feel and finish on the skin. The formulations improve the look and feel (e.g., radiance, glow, texture, smoothness of the skin). Additionally, use, including repeated use, of formulations of the present invention smooths and reduces the look of fine-lines, wrinkles and/or sagging.

Formulations of the present invention can improve symptoms of aging and skin dryness, including for example, skin dullness, loss of elasticity, lack of radiance, exaggerated lines and wrinkles, spider vessels, blotchiness, scaliness, itchiness, or any other symptom associated with dry skin. For example, "marionette" lines, smile lines, deep nasolabial fold lines, crow's feet, fine lines/wrinkles, vertical lines between the eyebrows, horizontal forehead lines, sagging thin/frail skin, and skin redness may be improved using formulations of the present invention. Additionally, pain or swelling of skin may be reduced using formulations of the present invention.

The present invention provides formulations that improve delivery of an active agent to and/or and through the surface layers of the skin, as compared with conventional skin care products. Improved delivery includes improved uptake, improved penetration or improved retention of a formulation, or any combination thereof as compared with conventional skin care products. Improved delivery also includes delivery of a formulation that is superior to conventional skin care products in its ability to reduce adverse effects of dry skin, aging or both, or reduce or reverse fine lines, sagging skin, wrinkles, or any combination thereof.

The present invention includes formulations comprising a dimethyl isosorbide, an oleic acid, and InvisaSkin®, where InvisaSkin® includes InvisaSkin RB®, InvisaSkin DS®, or both, both of which are proprietary compositions of Grant Industries (Elmwood Park, N.J.). It has been found that dimethyl isosorbide combined with oleic acid is believed to be effective at opening pores in the skin thereby enhancing uptake, penetration, or both by an active agent where an active agent is one that may moisturize skin, may reduce fine lines, wrinkles, and sagging skin, or any combination thereof.

Further, without being bound by theory, the inclusion of InvisaSkin® together with oleic acid and dimethyl isosorbide provides enhanced beneficial effects and facilitates better penetration and/or retention of an active agent. The look and feel of the skin is improved to an unexpectedly enhanced degree upon use of the present formulations as compared with use of conventional skin care products. The effects of this combination and the benefits to the skin are unexpected and more than additive.

The anti-aging effects of the present formulations are unexpectedly strong, with the present formulations providing better than expected positive results, including for example, better moisturization of skin, a reduction in fine lines and wrinkles and sagging skin, an improved look, feel, texture and radiance of skin as compared with results from conventional skin care products. Formulations of the present invention provide an improved look, feel, texture and radiance of skin through a decrease in fine lines and wrinkles, an increase in elasticity, flexibility or both, an improvement in skin moisture content, and increased skin brightness, clarity, uniformity or any combination thereof. The present formulations may also provide a reduction of pain or swelling of skin, where the active agent has anti-microbial, analgesic, or anti-inflammatory activity.

Formulations of the present invention optionally further include one or more active agent, or an active agent may be delivered separately from a formulation of the present invention. An active agent is one that may moisturize skin, may reduce fine lines, wrinkles, and sagging skin, may otherwise improve the look, feel, texture, or radiance of skin, or may achieve any such combination of effects. An active agent may also act as an antimicrobial, reduce pain, inhibit redness, inhibit swelling, or have any combination of such effects.

An active agent may be selected from the group consisting of an antioxidant, a vitamin, a plant extract, an anti-aging peptide, an anti-wrinkle peptide, a UV absorber and/or NO MOBO BT. In an embodiment, a formulation of the present invention includes NO MOBO BT as an active agent. Other exemplary active agents include pharmaceuticals with antimicrobial, antihistamine, anti-inflammatory, anti-stress, anti-redness, anti-pigmentation, or analgesic activity.

Other exemplary, non-limiting active agents include water soluble compounds that reduce or reverse fine-lines, wrinkles and/or skin sagging and/or hydrate or moisturize the skin and improve the look and feel of skin. For example, active agents may include niacinimide, glabridin, mu conotoxin peptides, e.g., mu-conotoxin CnIIIc peptide, (e.g., XEP-018 or XEP-030, BC Research Company), plant and/or algae extracts, e.g., *Betula alba* bark extract, *Boswellia serrate* resin extract and *Centella asiatica* extract, algae extract, *Albizia julibrissin* bark extract, *Magnolia grandiflora* bark extract, as well as peptides routinely used in the cosmetic industries, e.g. an anti-wrinkle peptide(s) and/or a myorelaxant peptide(s), anti-oxidants, pH adjusters, and ultraviolet light (UV) absorbing agents. Other active agents include, by way of non-limiting example, NO MOBO BT, White Birch BT (e.g., Biocomponent Research, Elmwood Park, N.J.), Algogen 2000 (commercially available through Grant Industries), BEAUTIFEYE™ (commercially available through Sederma) and *Magnolia* Super Extract (commercially available through Premier Specialties, Inc.), conotoxins, e.g., µ-conotoxin CnIIIc and X-50 (commercially available through Infinitec Barcelona), a pamitoyl-heptapeptide or a pantothenic acid-heptapeptide-Cu.

The amount of active agent in the formulation may be any amount that is sufficient to reduce the adverse effects of dry skin, aging, or both. Preferable active agents include niacinamide, glabridin, and mu Conotoxin CnIIIc (XEP-030 or XEP-018). The amount of the active may be for example about 0.01% to about 10%, or about 0.01% to about 5%, or about 0.01% to about 1% or about 0.01% to about 0.05% by weight of the formulation. For example, mu conotoxins may be present in the formulation at a concentration of, e.g., about 0.05 μM to 5 μM, 0.05 μM to 2.5 μM, 0.05 μM to 1 μM, 0.1 μM 0.5 μM, 0.1 μM to 0.3 μM, 0.25 μM to 0.35 μM or any other concentration that that is sufficient for the formulation to reduce the adverse effects of dry skin and aging.

The term "skin" includes outer surfaces of the body and can include hair and nails.

Formulations of the invention provide increased retention, concentration, or both of one or more active agents when applied topically to the skin as compared to other formulations that comprise dimethyl isosorbide and oleic acid without InvisaSkin® or formulations that comprise InvisaSkin® but do not comprise dimethyl isosorbide and oleic acid.

Because the combination of dimethyl isosorbide and oleic acid with InvisaSkin® increases retention, concentration, or both of one or more active agents topically applied to the skin, the formulations may also include less amounts of the active agent compared with conventional formulations in order to achieve similar effects, or both on the skin. In addition, by increasing the uptake, penetration, retention, or any combination thereof of an active agent, the active agent may be delivered more quickly to the skin and therefore act more quickly than other formulations comprising the same active agent. In addition, in an embodiment, formulations described herein may be administered less frequently than other formulations known in the art to alleviate the symptoms of aging and dry skin.

In formulations of the present invention, it is contemplated that oleic acid may be replaced with another short chain fatty acid (e.g., less than or equal to C16). In various embodiments, oleic acid may be replaced with lauric acid, octynylic acid, octanoic acid, myristic acid, palmitic acid, dodecanoic acid, or the like, or any combination thereof, including combinations with oleic acid.

In other embodiments, it is contemplated that dimethyl isosorbide may be replaced with propanediol, including any of 1,2-propanediol, 2,2-propanediol, 1,3-propanediol, or any combination thereof, including combinations with oleic acid.

Formulations of the present invention may also comprise any excipient known to the skilled artisan in an amount effective to confer a desired property, such as by way of non-limiting example, stability, flowability, solubility, spreadability, bulk, absorbability, penetrability, viscosity, pH, color, texture, sheen, fragrance, and the like.

By way of example, formulations may comprise water, an emulsifier, a stabilizer, an elastomer, a pH adjuster, or any combination thereof together with any other or no other optional ingredients herein.

Formulations of the present invention optionally include one or more elastomer (e.g., cyclopentasiloxane or Polysilicone-11 or mixtures thereof), pH adjuster, penetration enhancer, dimethicone (e.g., a low viscosity dimethicone), thickener (e.g., carbomer, sodium acrylate/sodium acryloyldimethyl taurate copolymer), emollient (e.g., isohexadecane), emulsifier (e.g., a carbomer such as carbopol ultrez 10 polymer, steareth-2, steareth-4, steareth-10, steareth-20, steareth-21, steareth-30, or Tween-20), salt, or any combination thereof.

Formulations of the present invention optionally comprise a non-ionic solvent, a fatty acid, or both. Formulations of the present invention optionally include one or more glycol compounds, carbomers, non-ionic surfactants, polysorbate surfactants (e.g., polysorbate 80, polysorbate 60, polysorbate 20), broad spectrum antimicrobials, sodium hyaluronates, white birch BT, NO MOBO BT, nonionic solvents, ALGOGEN 2000, central nervous system stimulants, nitrogenous organic acids, InvisaSkin®, vitamins, e.g., niacinimide, glabridin, mu conotoxin Cniiin peptide (XEP-030), isoflavonoids, BEAUTIFEYE™, proteins (including whey proteins), crosspolymer and copolymer complexes, low viscosity elastomer dispersions, elastomer powder emulsions, high viscosity silicones, squalanes, fatty acids, emollients, aqueous strong base solutions, natural or synthetic humectants, pre-neutralized polymers in an inverse emulsion, stabilizing/thickening agents, anti-wrinkle peptides, *Magnolia* Super Extract, myorelaxant peptides, peptides encapsulated in a liposome, e.g., X-50 (Infinitec Barcelona), polymer microspheres, UV absorbers, coloring agents, and fragrance agents.

In addition, the formulations described herein may comprise one or more of thickeners, polymers, copolymers, surfactants, antimicrobials, humectants, antioxidants, preservatives, plant and algae extracts, penetration enhancers, stimulants, amino acids, skin conditioners, wrinkle minimizer(s), elastomer(s), peptide(s), e.g., an anti-wrinkle peptide(s) and/or a myorelaxant peptide(s), moisturizers, dimethicones, salts and pH adjusters, dyes and fragrances. The formulations may also comprise a high viscosity silicone, squalane, a fatty acid, an emollient, an aqueous strong base solution, a synthetic humectant, a pre-neutralized polymer in an inverse emulsion, and/or a stabilizing/thickening agent.

Formulations of the present invention may also include, without limitation, $C_1$-$C_3$ alkyl parabens and phenoxyethanol, and ISP's Optiphen™ as preservatives, fatty esters, fatty alcohols, mineral oils, polymers and compolymers, e.g., carbopol ultrez 10 polymer, dimethylacrylamide/acrylic acid/polystyrene ethyl methacrylate copolymers, adipic acid/neopentyl glycol crosspolymer, hydroxypropyl methylcellulose and VP/VA copolymers, polyether siloxane copolymers, cyclopentasiloxane & polysilicone-11, docosahexanoic acid (DHA) and mixtures thereof as emollients.

As discussed, glycols, including propylene glycol and butylene glycol, may be used as humectants in the formulations of the present invention. As used herein, a humectant refers to an ingredient that acts in reducing loss of skin moisture. Additional humectants such as for example but not limited to, polyhydric alcohols such as glycerol, other polyalkylene glycols (e.g., dipropylene glycol, polypropylene glycol, and polyethylene glycol) and derivatives thereof, alkylene polyols and their derivatives, sorbitol, hydroxy sorbitol, hexylene glycol, 1,3-dibutylene glycol, 1,2,6-hexanetriol, ethoxylated glycerol, propoxylated glycerol, sodium hyaluronate, glycerin, and mixtures thereof may also be used as humectants.

Emulsifiers can also be added as additional ingredients in the formulations of the present invention and include, but are not limited to, dimethicone, polydimethylsiloxane, polysorbate 80, polysorbate 20 (Tween 20), stearic acid, cetyl alcohol, stearyl alcohol, steareth 2, steareth 20, steareth 21, acrylates/C10-30 alkyl acrylate crosspolymers, silicones, dimethylethanolamine (DMAE), phosphatidylcholine (PPC), docosahexanoic acid (DHA) and mixtures thereof. Preferred emulsifiers are steareth 21, sodium hyaluronate, Promulgen-D®. (a mixture of 75% cetostearyl alcohol and 25% ethoxylate cetostearyl alcohol sold by Amerchol Corp.), Arlacel™ 165 (Glyceryl Stearate and PEG-100 Stearate sold by Croda Inc.) silicone (Dow Corning®. 200 Fluid, 350 CST), dimethylaminoethanol, also known as DMAE, and Phospholipon® 90 G (phosphatidylcholine with 10% fatty acids sold by Phospholipid GmbH).

Stabilizers can also be added as additional ingredients in the formulations of the present invention and include, but are not limited to carbomers and glycols (e.g., carbopol ultrez 10 polymer, sodium acrylate/sodium acryloyldimethyl taurate copolymer, and pentylene glycol).

Preservatives can also be added as additional ingredients in the formulations of the present invention and include, but are not limited to benzoic acid, sodium benzoate, dehydroacetic acid, sodium dehydroacetate, isobutyl p-oxybenzoate, isopropyl p-oxybenzoate, butyl p-oxybenzoate, ethyl p-oxybenzoate, propyl p-oxybenzoate, benzyl p-oxybenzoate, methyl p-oxybenzoate, and phenoxyethanol.

Chelating agents can also be added as additional ingredients in formulations of the present invention. Exemplary chelating agents include, but are not limited to, ethylenediamine tetraacetic acid (EDTA) and derivatives and salts thereof, dihydroxyethyl glycine, tartaric acid, and mixtures thereof.

Antioxidants, which may be added to formulations of the present invention, include, but are not limited to, niacinamides, plant extracts, butylated hydroxy toluene (BHT); vitamin C and/or vitamin C derivatives, such as fatty acid esters of ascorbic acid, particularly ascorbyl palmitate; butylated hydroanisole (BHA); phenyl-a-naphthylamine; hydroquinone; propyl gallate; nordihydroquiaretic acid; vitamin E and/or derivatives of vitamin E, including tocotrienol and/or tocotrienol derivatives; calcium pantothenates; green tea extracts; mixed polyphenols; and mixtures of any of these. Particularly preferred antioxidants are those that provide additional benefits to the skin such as ascorbyl palmitate, sesame seed oil, alpha-lipoic acid, and Tocomin™ 50 (palm oil, tocotrienols, tocopherol).

Buffering or other pH-adjusting agents can be used in the formulations of the present invention in order to achieve a desired pH. A desired pH may be from about 5.0 to about 9.0, from about 6.0 to about 8.0, from about 6.5 to about 7.5. In other embodiments, a desired pH may also be about 5.0, 5.5, 6.0, 6.5, 7.0, 7.5, 8.0, 8.5 or 9.0. Typical buffering agents are chemically and physically stable agents commonly found in cosmetics, and can include compounds that are also adjunct ingredients such as citric acid, malic acid, and glycolic acid buffers.

Formulations of the present invention may also comprise routine cosmetic additives: pigments, colorants, biological active constituents (anti-age, anti-oily skin, brightening, whitening, anti-oxidants, etc.), sun filters, film-forming polymers, oils, fats, hydrating agents, emollients, solvents, surfactants, emulsifiers, stabilizers, vitamins, and/or preservatives, or other cosmetic excipients.

Formulations of the present invention may also comprise any one or more of the ingredients selected from the group consisting of carbopol ultrez 10 polymer, Steareth-21, Tween 20, diocide, sodium hyaluronate 2% aq. sol., WHITE BIRCH BT, NO MOBO BT, Algogen 2000, Caffeine, TEGO® COSMO C 100, niacinamide PC, Glabridin, mu Conotoxin CnIIIn peptide (XEP-030 or XEP-018), BEAU-TIFEYE™, Whey Protein Concentrate 80%, Aurasphere® N, Gransil GCM-5 (Grant Industries), Gransil EP-9 (Grant Industries), Gransil 530 (Grant Industries), Phytolane LS, Dimethicone 20 CST, KOH 10% aq. sol., Hydrolite-5, Simulgel EG, Argireline® NP, *Magnolia* Super Extract, X-50 0.10% aq. sol., CL-2080, Timiron Super Red, Red No. 4 in butylene glycol sol. 1%, fragrance.

Ingredients in each formulation provided herein are provided by weight percentage, unless otherwise specified. Dimethyl isosorbide, oleic acid, and InvisaSkin® may be included in any form and in any weight percent understood by the skilled artisan within the spirit and scope of the present invention.

A formulation of the present invention may comprise about 1% to 20%, about 2% to 10%, about 3 to 6%, or about 6% dimethyl isosorbide, may comprise about 0.1% to 20%, about 0.5% to 10%, about 0.5% to 5% or about 0.5% oleic acid, and may comprise about 0.5 to 10%, about 1% to 5%, about 1% to 3%, or about 1.5% InvisaSkin®. Water, including deionized water, may also optionally be included in any amount from about 5% to about 90%.

In another embodiment, the present invention includes and provides a formulation, where the formulation comprises about 1% to 20%, about 2% to 10%, or about 6% dimethyl isosorbide, comprises about 0.1% to 20%, about 0.5% to 10%, about 0.5% to 5% or about 0.5% oleic acid, and comprises about 0.5 to 10%, about 1% to 5%, about 1% to 3%, or about 1.5% InvisaSkin® RB®, about 5% to 90% water and one or more active agents.

In another embodiment, the present invention includes and provides a formulation, where the formulation comprises about 6% dimethyl isosorbide, about 0.5% oleic acid, and about 1.5% InvisaSkin® RB.

In an embodiment, a formulation of the present invention comprises about 1-20% dimethyl isosorbide, about 0.1-20% oleic acid, and about 0.5-10% InvisaSkin®. In another embodiment, a formulation of the present invention comprises about 2-10% dimethyl isosorbide, about 0.5-10% oleic acid, and about 1-5% InvisaSkin®. In a further embodiment, a formulation of the invention comprises about 6% dimethyl isosorbide, about 0.5% oleic acid, and about 1.5% InvisaSkin®. For example, the present invention includes and provides formulations comprising about 1-20% dimethyl isosorbide, about 0.1-1% oleic acid, about 0.5-4% InvisaSkin RB®, and about 0.5-5% NO MOBO BT. In another embodiment, a formulation comprises about 1-20% dimethyl isosorbide, about 0.1-1% oleic acid, about 0.5-4% InvisaSkin®, and about 0.5-5% NO MOBO BT.

In an embodiment, a formulation of the present invention comprises about 1-20% dimethyl isosorbide, about 0.1-20% oleic acid, and about 0.5-10% InvisaSkin RB®. In another embodiment, a formulation of the present invention comprises about 2-10% dimethyl isosorbide, about 0.5-10% oleic acid, and about 1-5% InvisaSkin RB®. In a further embodiment, a formulation of the invention comprises about 6% dimethyl isosorbide, about 0.5% oleic acid, and about 1.5% InvisaSkin RB®. For example, the present invention includes and provides formulations comprising about 1-20% dimethyl isosorbide, about 0.1-1% oleic acid, about 0.5-4% InvisaSkin RB®, and about 0.5-5% NO MOBO BT. In another embodiment, a formulation comprises about 1-20% dimethyl isosorbide, about 0.1-1% oleic acid, about 0.5-4% InvisaSkin RB®, and about 0.5-5% NO MOBO BT.

In another embodiment, a formulation comprises about 5-90% deionized water, about 0.1-0.5% carbopol ultrez 10 polymer, about 0.5-3% Steareth-21, about 0.5-3% Tween 20, about 0.5-2% diocide, about 0.5-3% sodium hyaluronate 2% aq. sol., about 0.5-4% white birch BT, about 0.5-5% NO MOBO BT, about 1-20% dimethyl isosorbide, 1-10% Algogen 2000, about 0.05-0.3% Caffeine, about 0.5-3% TEGO® COSMO C 100, about 0.5-4% InvisaSkin RB®, about 0.5-3% niacinamide PC, about 0.01-1% Glabridin, about 0.5-3% BEAUTIFEYE™, about 0.5-3% Whey Protein Concentrate 80%, about 8-18% Aurasphere® N, about 5-18% Gransil GCM-5, about 5-15% Gransil EP-9, about 1-5% Gransil 530, about 1-4% Phytolane LS, about 0.1-1% oleic acid, about 0.5-5% Dimethicone 20 CST, about 1-5% KOH 10% aq. sol., about 1-5% Hydrolite-5, about 0.1-2% Simulgel EG, about 2-8% Argireline® NP, about 0.05-2% *Magnolia* Super Extract, about 2-8% XEP-018, about 0.5-3% X-50 0.10% aq. sol., about 2-8% CL-2080, about 1-3% Timiron Super Red, about 0.01-0.08% Red No. 4 in butylene glycol sol. 1%, about 0.1-0.6% fragrance.

In a further embodiment, the present invention includes and provides a formulation comprising about 1 to 20% dimethyl isosorbide, about 0.5% to 10% oleic acid, about 0.5% to 10% InvisaSkin® RB, and about 5 to 10% deionized water and optionally further comprising any one or more of ingredients selected from the group consisting of about 0.1 to 0.5% carbopol ultrez 10 polymer, about 0.5 to 3% Steareth-21, about 0.5 to 3% Tween 20, about 0.5 to 2% diocide, about 0.5 to 3% sodium hyaluronate 2% aq. sol., about 0.5 to 4% white birch BT, about 0.5 to 5% NO MOBO BT, about 1 to 10% Algogen 2000, about 0.05 to 0.3% Caffeine, about 0.5 to 3% TEGO® COSMO C 100, about 0.5 to 3% niacinamide PC, about 0.01 to 1% Glabridin, about 0.01 to 5% of XEP-030 (mu Conotoxin Cniiin peptide), about 0.5 to 3% BEAUTIFEYE™, about 0.5 to 3% Whey Protein Concentrate 80%, about 8 to 18% Aurasphere® N, about 5 to 18% Gransil GCM-5, about 5 to 15% Gransil EP-9, about 1 to 5% Gransil 530, about 1 to 4% Phytolane LS, about 0.5 to 5% Dimethicone 20 CST, about 1 to 5% KOH 10% aq. sol., about 1 to 5% Hydrolite-5, about 0.1 to 2% Simulgel EG, about 2 to 8% Argireline® NP, about 0.05 to 2% *Magnolia* Super Extract, about 2 to 8% XEP-018, about 0.5 to 3% X-50 0.10% aq. sol., about 2 to 8% CL-2080, about 1-3% Timiron Super Red, about 0.01 to 0.08% Red No. 4 in butylene glycol sol. 1%, about 0.1 to 0.6% fragrance.

In another embodiment, a formulation comprises about 6% deionized water, about 0.3% carbopol ultrez 10 polymer, about 1.5% Steareth-21, about 1% Tween 20, about 1% diocide, about 1% sodium hyaluronate 2% aq. sol., about 2% white birch BT, about 2% NO MOBO BT, about 6% dimethyl isosorbide, about 5% Algogen 2000, about 0.1% Caffeine, about 1% TEGO® COSMO C 100, about 1.5% InvisaSkin RB®, about 1% niacinamide PC, about 0.05% Glabridin, about 1% BEAUTIFEYE™, about 1% Whey Protein Concentrate 80%, about 13% Aurasphere® N, about 11% Gransil GCM-5, about 10% Gransil EP-9, about 2% Gransil 530, about 2% Phytolane LS, about 0.5% oleic acid, about 2% Dimethicone 20 CST, about 2% KOH 10% aq. sol., about 3% Hydrolite-5, about 0.5% Simulgel EG, about 5% Argireline® NP, about 0.1% *Magnolia* Super Extract, about 5% XEP-018, about 1% X-50 0.10% aq. sol., about 5% CL-2080, about 2% Timiron Super Red, about 0.04% Red No. 4 in butylene glycol sol. 1%, about 0.35% fragrance.

In a further embodiment, the present invention includes and provides a formulation comprising about 6% dimethyl isosorbide, about 0.5% Oleic acid, about 1.5% InvisaSkin® RB, and about 6% deionized water, and optionally further comprising any one or more of ingredients selected from the group consisting of about 0.3% carbopol ultrez 10 polymer, about 1.5% Steareth-21, about 1% Tween 20, about 1% diocide, about 1% sodium hyaluronate 2% aq. sol., about 2% white birch BT, about 2% NO MOBO BT, about 5% Algogen 2000, about 0.1% Caffeine, about 1% TEGO® COSMO C 100, about 1% niacinamide PC, about 0.05% Glabridin, about 0.5% XEP-030 (mu Conotoxin CnIIIn peptide), about 1% BEAUTIFEYE™, about 1% Whey Protein Concentrate 80%, about 13% Aurasphere® N, about 11% Gransil GCM-5, about 10% Gransil EP-9, about 2% Gransil 530, about 2% Phytolane LS, about 2% Dimethicone 20 CST, about 2% KOH 10% aq. sol., about 3% Hydrolite-5, about 0.5% Simulgel EG, about 5% Argireline® NP, about 0.1% *Magnolia* Super Extract, about 5% XEP-018 (mu Conotoxin CnIIIn peptide), about 1% X-50 0.10% aq. sol., about 5% CL-2080, about 2% Timiron Super Red, about 0.04% Red No. 4 in butylene glycol sol. 1%, about 0.35% fragrance.

In another embodiment, the present invention provides a formulation comprising a mixture of 13 phases, identified as Phases A-M, which may be mixed in any order and ingredients from any Phase added to another Phase, wherein Phase A comprises 5-90% deionized water, about 0.1-0.5% carbopol ultrez 10 polymer, about 0.5-3% Steareth-21, about 0.5-3% Tween 20, about 0.5-2% diocide, about 0.5-3% sodium hyaluronate 2% aq. sol., about 0.5-4% white birch BT, about 0.5-5% NO MOBO BT, about 1-20% dimethyl isosorbide, about 2-10% Algogen 2000, about 0.05-0.3% Caffeine, about 0.5-3% TEGO® COSMO C 100, about 0.5-10% InvisaSkin RB®, about 0.5-3% niacinamide PC, about 0.01-1% Glabridin, about 0.5-3% BEAUTIFEYE™, Phase B comprises about 0.5-3% Whey Protein Concentrate 80%, Phase C comprises about 8-18% Aurasphere® N and about 5-18% Gransil GCM-5, Phase D comprises about 5-15% Gransil EP-9,
Phase E comprises about 1-5% Gransil 530, about 1-4% Phytolane LS, about 0.1-1% Oleic acid, and about 0.5-5% Dimethicone 20 CST,
Phase F comprises about 1-5% KOH 10% aq. sol.,
Phase G comprises about 1-5% Hydrolite-5,
Phase H comprises about 0.1-2% Simulgel EG,
Phase I comprises about 2-8% Argireline® NP and about 0.05-2% *Magnolia* Super Extract,
Phase J comprises about 2-8% XEP-018 and about 0.5-3% X-50 0.10% aq. sol.,
Phase K comprises about 2-8% CL-2080, and about 1-3% Timiron Super Red,
Phase L comprises about 0.01-0.08% Red No. 4 in butylene glycol sol. 1%, and wherein
Phase M comprises about 0.1-0.6% fragrance.

While the composition of each Phase and the order of addition of Phases may vary, in a preferred embodiment, dimethyl isosorbide is combined with InvisaSkin® in the water phase.

In another embodiment, the present invention provides a formulation comprising a mixture of 13 phases, identified as Phases A-M, which may be mixed in any order and ingredients from any Phase added to another Phase, wherein Phase A comprises about 6% deionized water, about 0.3% carbopol ultrez 10 polymer, about 1.5% Steareth-21, about 1% Tween 20, about 1 diocide, about 1% sodium hyaluronate 2% aq. sol., about 2% white birch BT, about 2% NO MOBO BT, about 6% dimethyl isosorbide, about 5% Algogen 2000, about 0.1% Caffeine, about 1% TEGO® COSMO C 100, about 1.5% InvisaSkin RB, about 1% niacinamide PC, about 0.05% Glabridin, about 1% BEAUTIFEYE™,
Phase B comprises about 1% Whey Protein Concentrate 80%,
Phase C comprises about 13% Aurasphere® N and about 11% Gransil GCM-5,
Phase D comprises about 10% Gransil EP-9,
Phase E comprises about 2% Gransil 530, about 2% Phytolane LS, about 0.5% Oleic acid, and about 2% Dimethicone 20 CST,
Phase F comprises about 2% KOH 10% aq. sol.,
Phase G comprises about 3% Hydrolite-5,
Phase H comprises about 0.5% Simulgel EG,
Phase I comprises about 5% Argireline® NP and about 0.1% *Magnolia* Super Extract,
Phase J comprises about 5% XEP-018 and about 1% X-50 0.10% aq. sol.,
Phase K comprises about 5% CL-2080, and about 2% Timiron Super Red,
Phase L comprises about 0.04% Red No. 4 in butylene glycol sol. 1%, and wherein
Phase M comprises about 0.35% fragrance.

While the composition of each Phase and the order of addition of Phases may vary, in a preferred embodiment, dimethyl isosorbide is combined with InvisaSkin® in the water phase.

The present invention also includes and provides methods for administration of an active agent to skin, where such methods may include methods of improved delivery, which increase penetration of an active agent into the skin as compared with conventional skin care products. Such methods provide many positive results, including improving or enhancing skin hydration or reducing skin conditions associated with aging, dryness or both. For example, the present methods may provide a reduction in fine lines and wrinkles, an increase in elasticity, flexibility or both, an improvement in skin moisture content, and an increased skin brightness, clarity, uniformity or any thereof. The present methods may also improve the health of skin or reduce pain or swelling of skin.

In an embodiment, the invention includes and provides a method for delivering an active agent to skin comprising applying a formulation described herein to the skin of a subject. The present invention further includes and provides methods of ameliorating the signs of aging and/or skin dryness including administering any of the formulations described herein by applying the formulation topically and allowing the formulation to remain on the skin without washing the skin for sufficient time such that symptoms and/or skin dryness is ameliorated.

By way of non-limiting example, in the methods of the present invention, a formulation may be allowed to remain on the skin without washing or applying any other agent for a few seconds, at least 1 minute, at least 10 minutes, at least 1 hour, or overnight.

In an embodiment, a formulation of the present invention is applied to clean, dry (i.e., non-wet) skin. In another embodiment, a formulation is applied to affected areas, where affected areas may include dry skin, dull skin, wrinkled skin, reddened skin, blotchy skin, or any combination thereof. In a further embodiment, a formulation of the present invention is applied to affected areas of clean, dry (i.e., non-wet) skin. The invention includes a method for improving texture and appearance of dry or aging skin comprising applying a formulation described herein to the skin of a subject. The present invention also includes methods of reducing fine lines, wrinkles, or both. The present invention includes methods of increasing elasticity/flexibility of skin. The present invention also includes methods of increasing skin brightness or clarity.

The present invention also includes methods of ameliorating skin dryness and/or reducing the size of pores in the skin by administering a formulation of the present invention. Ameliorating skin dryness refers to reducing skin dryness by any amount as compared with skin dryness prior to amelioration. Likewise, ameliorating skin dryness includes increasing skin hydration by any amount as compared with skin hydration prior to amelioration.

Measurement of reduction in skin dryness or increase in skin hydration or decrease in pore size can be accomplished in any manner known to the skilled artisan. For example, conventional modes of measuring skin hydration or pore size such as simple observation, i.e., visualization by a physician or other person skilled in observation of the skin may be used. Alternatively, in order to assess reduction in skin dryness or increase in skin hydration, near IR imaging, electronic methods based on conductance or capacitance may be used to measure skin hydration before and after applying a formulation of the present invention. Reduction in skin dryness or increase in skin hydration or reduction in pore size can also be assessed by a reduction in symptoms of skin dryness and/or increase is skin luminosity as reported by a person to whom a formulation is administered.

It is envisioned that formulations of the present invention can be administered by topical application in the form of a solution, serum, cream, ointment, paste, lotion, gel, jelly, suspension, emulsion, aerosol, foam, spray, transdermal patch, or the like and can be added to any other chemical formulation or product, such as for example a cosmetic product, for delivery to the skin. By way of non-limiting example, formulations of the present invention can be added to make up products such as foundations, skin creams, lipsticks, rouges, and the like. Formulations can also be added to self-tanning or toning products, cleansers, sunscreens, acne treatment products, or any other product intended for delivery to the skin. In some cases, addition of a formulation of the present invention to another chemical formulation or product provides additional therapeutic effects related to reduction of skin dryness and increase in skin hydration. In another embodiment, a formulation of the present invention may be administered alone. In another embodiment, more than one formulation according to the present invention (i.e., two formulations, three formulations, four or more formulations) may be combined in a single topical administration form.

In an embodiment, the formulation is administered in a controlled delivery form. For example, the formulation can release active agents over time or under specified pH conditions.

In an embodiment, a formulation of the present invention forms a film or layer on the skin so as to provide resistance to washing off by immersion in water or by perspiration and/or aid in the percutaneous delivery of the active agent(s).

In order to achieve desired timing, efficacy and the like for administration, optional additional carriers, adjuvants, thickeners, excipients, etc. can be used. By way of non-limiting example, thickening agents such as gums or other forms of hydrophilic colloids can be used. The inclusion of other additional ingredients commonly found in skin care compositions and cosmetics, such as, for example, tinting agents, emollients, skin conditioning agents, emulsifying agents, humectants, preservatives, antioxidants, perfumes, chelating agents, etc., is contemplated, provided that any other additional ingredients are physically and chemically compatible with other components of the formulations of the invention.

Formulations of the present invention can be administered at any interval conventionally used for moisturizing skin. For example, in an embodiment, formulations can be administered as desired to alleviate symptoms of skin dryness. In alternative embodiments, formations of the present invention can be administered once per week, once per two days, once daily, twice daily, three times daily, four times daily, five times daily, six times daily, seven times daily, eight times daily, nine times daily or ten times daily. Formulations can also be administered at least once daily, at least twice daily, at least three times daily, at least four times daily, at least five times daily, at least six times daily, at least seven times daily, at least eight times daily, at least nine times daily or at least ten times daily. In various other embodiments, formulations can be administered not more than once per week, not more than once per two days, not more than once per day, not more than twice daily, not more than three times daily, not more than four times daily, not more than five times daily, not more than six times daily, not more than seven times daily, not more than eight times daily, not more than nine times daily or not more than ten times daily.

Topical formulations according to the present invention are intended to be applied to and absorbed by skin. After treatment, any one or more of decreased inflammation, irritation, and erythema of the skin, or increased skin elasticity and suppleness can be observed. For example, any combination of "marionette" lines, smile lines, deep nasolabial fold lines, crow's feet, fine lines/wrinkles, vertical lines between the eyebrows, horizontal forehead lines, sagging thin/frail skin, skin redness and dullness, or skin itchiness are reduced. Administering formulations of the present invention is expected to improve the appearance of skin, and can prevent or treat skin aging, dryness, redness, scaliness, dullness, loss of elasticity, or lack of radiance.

Methods of treatment can be used to prevent or retard the appearance of spider vessels or red blotchiness associated with menopausal skin. In another embodiment, treatments may be used to prevent or treat exaggerated lines and wrinkles.

In an embodiment, administration of a formulation of the present invention is accomplished in association with a dermatologically acceptable carrier, and in a preferred embodiment, one in which the formulation is soluble per se or is effectively solubilized (e.g., as an emulsion or microemulsion). Where employed, a carrier is inert in the sense of not bringing about a deactivation or chemical reaction of the formulation.

In accordance with methods of the invention, a topical formulation is generally applied topically to the skin such as the face or hands, in particular the forehead, cheeks, or contour of an eye (periocular region), crow's feet, the area below the eye (bag), eyelids, neck, feet, legs, arms, forearms, or any other dry area of the body, at predetermined intervals, often as a moisturizer, lotion, or cream. In an embodiment, gradual improvement of symptoms of dryness is noted with each successive application. For example, effects can be observed after administration for one day, administration for two days, administration for three days, administration for four days, administration for five days, administration for one week, at least one week, two weeks, at least two weeks, one month, at least one month.

Symptoms of aging and skin dryness that may be improved by methods of administering formulations of the present invention include for example, skin dullness, loss of elasticity, lack of radiance, exaggerated lines and wrinkles, spider vessels, red blotchiness, scaliness, itchiness, or any other symptom associated with dry skin. For example, "marionette" lines, smile lines, deep nasolabial fold lines, crow's feet, fine lines/wrinkles, vertical lines between the eyebrows, horizontal forehead lines, sagging thin/frail skin, overall skin redness may be improved using methods of administering formulations of the present invention.

Additionally, methods of administering formulations of the present invention may improve uptake, penetration, retention or any combination thereof by an active agent as compared with conventional skin care products.

In an embodiment, formulations described herein may be administered less frequently than other formulations known in the art to alleviate the symptoms of aging and dry skin. In another embodiment, formulations of the present invention that are administered may include less active agent than other formulations comprising the same active agent to achieve similar concentrations of the active agent, effect, or both on the skin. In another embodiment, administered formulations may act more quickly than other formulations comprising the same active agent.

In further embodiments, administered formulations may provide increased retention, concentration, or both as compared to other formulations that comprise dimethyl isosorbide and oleic acid without InvisaSkin® or formulations that comprise InvisaSkin® but do not comprise dimethyl isosorbide and oleic acid. As discussed herein, the combination of dimethyl isosorbide, oleic acid, and InvisaSkin® provides a more than additive effect in allowing for improved penetration and retention of agents as compared with conventional products.

Methods for delivery of an active agent to skin as provided herein include administering any formulation apparent to the skilled artisan on the basis of the present disclosure. By way of non-limiting example, the present invention includes and provides methods for improved delivery of an active agent to skin, where the formulation administered includes about 1-20% dimethyl isosorbide, about 0.1-20% oleic acid, and about 0.5-10% InvisaSkin®. The present invention also includes and provide methods where the formulation includes about 2-10% dimethyl isosorbide, about 0.5-10% oleic acid, and about 1-5% InvisaSkin®, or alternatively the formulation may include about 1-20% dimethyl isosorbide, about 0.1-1% oleic acid, about 0.5-4% InvisaSkin®, and about 0.5-5% NO MOBO BT. The administered formulation may include about 6% dimethyl isosorbide, about 0.5% oleic acid, and about 1.5% InvisaSkin®.

By way of additional example, the present invention includes and provides methods for improved delivery of an active agent to skin, where the formulation administered includes about 1-20% dimethyl isosorbide, about 0.1-20% oleic acid, and about 0.5-10% InvisaSkin RB®. The present invention also includes and provide methods where the formulation includes about 2-10% dimethyl isosorbide, about 0.5-10% oleic acid, and about 1-5% InvisaSkin RB®, or alternatively the formulation may include about 1-20% dimethyl isosorbide, about 0.1-1% oleic acid, about 0.5-4% InvisaSkin RB®, and about 0.5-5% NO MOBO BT. The administered formulation may include about 6% dimethyl isosorbide, about 0.5% oleic acid, and about 1.5% InvisaSkin RB®.

The present invention also includes and provides methods of making formulations of the present invention. The present invention includes a method of making a formulation, the method comprising combining dimethyl isosorbide, oleic acid, and InvisaSkin®. In an embodiment, a method of making a formulation of the present invention comprises combining dimethyl isosorbide, oleic acid, and InvisaSkin® and heating to about 60° C.-110° C. or about 75° C.-80° C.; and then cooling to room temperature, or to about 22° C.-60° C. or about 50° C. pH may be adjusted to about 7.

Methods of making other formulations provided herein comprise adding optional ingredients as provided herein to produce the formulations provided herein, and adjusting the pH to about 7.

In various embodiments, one or more glycol acting as a humectant, one or more agent (e.g., NO MOBO BT), or both are also combined in making the formulation. Ingredients in any of the formulations may be combined in order to make the formulations taught herein.

For example, the present methods of making a formulation include combining dimethyl isosorbide, oleic acid, and InvisaSkin RB®, water, and optionally an emulsifier, a stabilizer, or both to form an emulsified formulation.

In an embodiment, in making a formulation of the present invention, the ingredients are mixed to homogeneity. In other embodiments, the ingredients form an emulsion or suspension.

In an embodiment, dimethyl isosorbide, oleic acid, InvisaSkin® RB, and optionally water, and optionally an emulsifier and/or stabilizer, may be heated to about 60° C.-110° C. or about 75° C.-80° C.; and then cooled to room temperature, or to about 22° C.-60° C. or about 50° C. The formulation may further comprise one or more additional ingredients including a carbomer, a non-ionic surfactant, a polysorbate solvent, a broad spectrum antimicrobial, sodium hyaluronate, white birch BT, NO MOBO BT, a non-ionic solvent, Algogen 2000, a central nervous system stimulant, a nitrogenous organic acid, a vitamin B, an isoflavonoid, and BEAUTIFEYE™. The additional ingredients may be added before or after the dimethyl isosorbide, oleic acid, InvisaSkin® RB, and water, optionally an emulsifier and/or stabilizer, are combined and heated to form an emulsified formulation, e.g., the additional ingredients may be added after cooling to about 50° C. and then further cooled to room temperature.

The present invention includes and provides a method of making a formulation, the method comprising:
combining dimethyl isosorbide, InvisaSkin® RB, water, a carbomer, a non-ionic surfactant, a polysorbate solvent, a broad spectrum antimicrobial, sodium hyaluronate, white birch BT, NO MOBO BT, a non-ionic solvent, Algogen 2000, a central nervous system stimulant, a nitrogenous organic acid, a vitamin B, an isoflavonoid, and BEAUTIFEYE™ to produce a Phase A;
heating the Phase A to about 75-80° C.;
cooling the Phase A to about 50° C.;
mixing a Phase B with the Phase A, wherein the Phase B comprises a protein to produce a Phases A-B mixture;
mixing a Phase C comprising a crosspolymer and copolymer complex and a low viscosity elastomer dispersion, a Phase D comprising an elastomer powder emulsion, and a Phase E comprising a high viscosity silicone, a squalane, an oleic acid, and an emollient with the Phases A-B mixture to produce a Phases A-E mixture;
mixing a Phase F comprising an aqueous strong base solution with the Phases A-E mixture to produce a Phases A-G mixture;
mixing a Phase H comprising a stabilizing/thickening agent with the Phases A-G mixture to produce a Phases A-H mixture;
mixing a Phase I comprising an anti-wrinkle peptide and *Magnolia* Super Extract with the Phases A-H mixture to produce a Phases A-I mixture;
mixing a Phase J comprising a myorelaxant peptide and X-50 with the Phases A-I mixture to produce a Phases A-J mixture;
mixing a Phase K comprising a polymer microsphere and a coloring agent, with the Phases A-J mixture to produce a Phases A-K mixture;
mixing a Phase L comprising and a coloring agent with the Phases A-K mixture to produce a Phases A-L mixture;
mixing a Phase M comprising a fragrance with the Phases A-K mixture to produce a Phases A-M mixture; and
adjusting the pH of the Phases A-M mixture to about 7.

The order in which the Phases are mixed may vary and ingredients from any Phase may be added to another Phase. However, in a preferred embodiment, dimethyl isosorbide is combined with InvisaSkin® in the water phase.

The present invention includes and provides a method of making a formulation, the method comprising:
combining dimethyl isosorbide, InvisaSkin® RB, deionized water, carbopol ultrez 10 polymer, Steareth-21, Tween 20, diocide, sodium hyaluronate 2% aq. sol., white birch BT, NO MOBO BT, dimethyl isosorbide, Algogen 2000, Caffeine, TEGO® COSMO C 100, niacinamide PC, Glabridin, and BEAUTIFEYE™ to produce a Phase A;
heating the Phase A to about 75-80° C.;
cooling the Phase A to about 50° C.;
mixing a Phase B with the Phase A, wherein the Phase B comprises Whey Protein Concentrate 80% to produce a Phases A-B mixture;
mixing a Phase C comprising Aurasphere® N and Gransil GCM-5, a Phase D comprising Gransil EP-9, and a Phase E comprising Gransil 530, Phytolane LS, oleic acid, Dimethicone 20 CST with a Phases A-B mixture to produce a Phases A-E mixture;
mixing a Phase F comprising KOH 10% aq. sol. and a Phase G comprising Hydrolite-5 with the Phases A-E mixture to produce a Phases A-G mixture;

mixing a Phase H comprising Simulgel EG with the Phases A-G mixture to produce a Phases A-H mixture;

mixing a Phase I comprising Argireline® NP and *Magnolia* Super Extract with the Phases A-H mixture to produce a Phases A-I mixture;

mixing a Phase J comprising XEP-018 and X-50 0.10% aq. sol. with the Phases A-I mixture to produce a Phases A-J mixture;

mixing a Phase K comprising CL-2080, and Timiron Super Red with the Phases A-J mixture to produce a Phases A-K mixture;

mixing a Phase L comprising Red No. 4 in butylene glycol sol. 1% with the Phases A-K mixture to produce a Phases A-L mixture;

mixing a Phase M comprising fragrance with the Phases A-K mixture to produce a Phases A-M mixture; and adjusting the pH of the Phases A-M mixture to about 7.

The order in which the Phases are mixed may vary and ingredients from any Phase may be added to another Phase. However, in a preferred embodiment, dimethyl isosorbide is combined with InvisaSkin® in the water phase.

The present invention further includes and provides a method of making a formulation, the method comprising:

combining about 5-10% deionized water, about 0.1-0.5% carbopol ultrez 10 polymer, about 0.5-3% Steareth-21, about 0.5-3% Tween 20, about 0.5-2% diocide, about 0.5-3% sodium hyaluronate 2% aq. sol., about 0.5-4% white birch BT, about 0.5-5% NO MOBO BT, about 1-20% dimethyl isosorbide, about 1-10% Algogen 2000, about 0.05-0.3% Caffeine, about 0.5-3% TEGO® COSMO C 100, about 0.5-4% InvisaSkin RB, about 0.5-3% niacinamide PC, about 0.01-1% Glabridin, about 0.5-3% BEAUTIFEYE™ to produce a Phase A;

heating the Phase A to about 75-80° C.; cooling the Phase A to about 50° C.;

mixing a Phase B with the Phase A, wherein the Phase B comprises about 0.5-3% Whey Protein Concentrate 80% to produce a Phases A-B mixture;

mixing a Phase C comprising about 8-18% Aurasphere® N and about 5-18% Gransil GCM-5, a Phase D comprising about 5-15% Gransil EP-9, and a Phase E comprising about 1-5% Gransil 530, about 1-4% Phytolane LS, about 0.1-1% Oleic acid, and about 0.5-5% Dimethicone 20 CST with a Phases A-B mixture to produce a Phases A-E mixture;

mixing a Phase F comprising about 1-5% KOH 10% aq. sol. and a Phase G comprising about 1-5% Hydrolite-5 with the Phases A-E mixture to produce a Phases A-G mixture;

mixing a Phase H comprising about 0.1-2% Simulgel EG with the Phases A-G mixture to produce a Phases A-H mixture;

mixing a Phase I comprising about 2-8% Argireline® NP and about 0.05-2% *Magnolia* Super Extract with the Phases A-H mixture to produce a Phases A-I mixture;

mixing a Phase J comprising about 2-8% XEP-018 and about 0.5-3% X-50 0.10% aq. sol. with the Phases A-I mixture to produce a Phases A-J mixture;

mixing a Phase K comprising about 2-8% CL-2080 and about 1-3% Timiron Super Red with the Phases A-J mixture to produce a Phases A-K mixture;

mixing a Phase L comprising about 0.01-0.08% Red No. 4 in butylene glycol sol. 1% with the Phases A-K mixture to produce a Phases A-L mixture;

mixing a Phase M comprising about 0.1-0.6% fragrance with the Phases A-K mixture to produce a Phases A-M mixture; and adjusting the pH of the Phases A-M mixture to about 7.

The order in which the Phases are mixed may vary and ingredients from any Phase may be added to another Phase. However, in a preferred embodiment, dimethyl isosorbide is combined with InvisaSkin® in the water phase.

The present invention includes and provides a method of making a formulation, the method comprising:

combining about 6% deionized water, about 0.3% carbopol ultrez 10 polymer, about 1.5% Steareth-21, about 1% Tween 20, about 1 diocide, about 1% sodium hyaluronate 2% aq. sol., about 2% white birch BT, about 2% NO MOBO BT, about 6% dimethyl isosorbide, about 5% Algogen 2000, about 0.1% Caffeine, about 1% TEGO® COSMO C 100, about 1.5% InvisaSkin RB, about 1% niacinamide PC, about 0.05% Glabridin, and about 1% BEAUTIFEYE™ to produce a Phase A;

heating the Phase A to about 75-80° C.;
cooling the Phase A to about 50° C.;

mixing a Phase B with the Phase A, wherein the Phase B comprises about 1% Whey Protein Concentrate 80% to produce a Phases A-B mixture;

mixing a Phase C comprising about 13% Aurasphere® N and about 11% Gransil GCM-5, a Phase D comprising about 10% Gransil EP-9, and a Phase E comprising about 2% Gransil 530, about 2% Phytolane LS, about 0.5% oleic acid, about 2% Dimethicone 20 CST with a Phases A-B mixture to produce a Phases A-E mixture;

mixing a Phase F comprising about 2% KOH 10% aq. sol. and a Phase G comprising about 3% Hydrolite-5 with the Phases A-E mixture to produce a Phases A-G mixture;

mixing a Phase H comprising about 0.5% Simulgel EG with the Phases A-G mixture to produce a Phases A-H mixture;

mixing a Phase I comprising about 5% Argireline® NP and about 0.1% *Magnolia* Super Extract with the Phases A-H mixture to produce a Phases A-I mixture;

mixing a Phase J comprising about 5% XEP-018 and about 1% X-50 0.10% aq. sol. with the Phases A-I mixture to produce a Phases A-J mixture;

mixing a Phase K comprising about 5% CL-2080, and about 2% Timiron Super Red with the Phases A-J mixture to produce a Phases A-K mixture;

mixing a Phase L comprising about 0.04% Red No. 4 in butylene glycol sol. 1% with the Phases A-K mixture to produce a Phases A-L mixture;

mixing a Phase M comprising about 0.35% fragrance with the Phases A-K mixture to produce a Phases A-M mixture; and adjusting the pH of the Phases A-M mixture to about 7.

The order in which the Phases are mixed may vary and ingredients from any Phase may be added to another Phase. However, in a preferred embodiment, dimethyl isosorbide is combined with InvisaSkin® in the water phase.

The present invention further includes a formulation, which is prepared by mixing 13 phases, identified as Phases A-M.

In another embodiment, the present invention includes and provides a formulation, which is prepared by mixing 13 phases, identified as Phases A-M, where Phase A comprises 5-10% deionized water, about 0.1-0.5% carbopol ultrez 10 polymer, about 0.5-3% Steareth-21, about 0.5-3% Tween 20, about 0.5-2% diocide, about 0.5-3% sodium hyaluronate 2% aq. sol., about 0.5-4% white birch BT, about 0.5-5% NO MOBO BT, about 1%-20%, dimethyl isosorbide, about 1-10% Algogen 2000, about 0.05-0.3% Caffeine, about 0.5-3% TEGO® COSMO C 100, about 0.5-10%

InvisaSkin® RB, about 0.5-3% niacinamide PC, about 0.01-1% Glabridin, about 0.5-3% BEAUTIFEYE™, Phase B comprises about 0.5-3% Whey Protein Concentrate 80%, Phase C comprises about 8-18% Aurasphere® N and about 5-18% Gransil GCM-5, Phase D comprises about 5-15% Gransil EP-9, Phase E comprises about 1-5% Gransil 530, about 1-4% Phytolane LS, about about 0.5%-10% oleic acid, and about 0.5-5% Dimethicone 20 CST, Phase F comprises about 1-5% KOH 10% aq. sol., Phase G comprises about 1-5% Hydrolite-5, Phase H comprises about 0.1-2% Simulgel EG, Phase I comprises about 2-8% Argireline® NP and about 0.05-2% *Magnolia* Super Extract, Phase J comprises about 2-8% XEP-018 and about 0.5-3% X-50 0.10% aq. sol., Phase K comprises about 2-8% CL-2080, and about 1-3% Timiron Super Red, Phase L comprises about 0.01-0.08% Red No. 4 in butylene glycol sol. 1%, and where Phase M comprises about 0.1-0.6% fragrance.

In a further embodiment, the present invention includes and provides a formulation, which is prepared by mixing 13 phases, identified as Phases A-M, where Phase A comprises about 6% deionized water, about 0.3% carbopol ultrez 10 polymer, about 1.5% Steareth-21, about 1% Tween 20, about 1 diocide, about 1% sodium hyaluronate 2% aq. sol., about 2% white birch BT, about 2% NO MOBO BT, about 6% dimethyl isosorbide, about 5% Algogen 2000, about 0.1% Caffeine, about 1% TEGO® COSMO C 100, about 1.5% InvisaSkin RB, about 1% niacinamide PC, about 0.05% Glabridin, about 1% BEAUTIFEYE™, Phase B comprises about 1% Whey Protein Concentrate 80%, Phase C comprises about 13% Aurasphere® N and about 11% Gransil GCM-5, Phase D comprises about 10% Gransil EP-9, Phase E comprises about 2% Gransil 530, about 2% Phytolane LS, about 0.5% Oleic acid, and about 2% Dimethicone 20 CST, Phase F comprises about 2% KOH 10% aq. sol., Phase G comprises about 3% Hydrolite-5, Phase H comprises about 0.5% Simulgel EG, Phase I comprises about 5% Argireline® NP and about 0.1% *Magnolia* Super Extract, Phase J comprises about 5% XEP-018 and about 1% X-50 0.10% aq. sol., Phase K comprises about 5% CL-2080, and about 2% Timiron Super Red, Phase L comprises about 0.04% Red No. 4 in butylene glycol sol. 1%, and wherein Phase M comprises about 0.35% fragrance.

The following examples further describe and demonstrate embodiments within the scope of the present invention. The examples are given solely for the purpose of illustration and are not to be construed as any limitation of the present invention, as it is contemplated that many variations are possible without departing from the spirit and scope of the invention.

EXAMPLES

Example 1

An exemplary formulation of the present invention may be produces as follows:

| Phase | Ingredient | INCI | % |
|---|---|---|---|
| A | DEIONIZED WATER | Water | 6.060 |
|  | CARBOPOL ULTREZ 10 POLYMER | Carbomer | 0.300 |
|  | STEARETH-21 | Steareth-21 | 1.500 |
|  | TWEEN 20 | Polysorbate 20 | 1.000 |
|  | DIOCIDE | Caprylyl Glycol & Phenoxyethanol & Hexylene Glycol | 1.000 |
|  | SODIUM HYALURONATE, 2% AQ SOL. | Water & Sodium Hyaluronate | 5.000 |
|  | WHITE BIRCH BT* | Water & Betula Alba Bark Extract & Phenoxyethanol & Sodium Benzoate | 2.000 |
|  | NO MOBO BT | Water & Boswellia Serrate Resin Extract & Centella Asiatica Extract & Phenoxyethanol & Sodium Benzoate | 2.000 |
|  | GRANSOLVE DMI | Dimethyl Isosorbide | 6.000 |
|  | ALGOGEN 2000* | Water & Algae Extract & Glycine & Sucrose & N-Acetyl-D-Glucosamine | 5.000 |
|  | CAFFEINE | Caffeine | 0.100 |
|  | TEGO ® COSMO C 100 | Creatine | 1.000 |
|  | InvisaSkin RB ® | Water & Dimethylacrylamide/Acrylic Acid/Polystyrene Ethyl Methacrylate Copolymer & Oryza Sativa (Rice) Bran Extract & Phenoxyethanol & Sodium Benzoate | 1.500 |
|  | NIACINAMIDE PC | Niacinamide | 1.000 |
|  | GLABRIDIN | Glabridin | 0.050 |
|  | BEAUTIFEYE (TM) | Glycerin & Albizia Julibrissin Bark Extract & Darutoside | 1.000 |
| B | WHEY PROTEIN CONCENTRATE, 80% | Whey Protein | 1.000 |
| C | AURASPHERE ® N | Adipic Acid/Neopentyl Glycol Crosspolymer & Water & Aminodimethicone & Dimethicone & Hydroxypropyl Methylcellulose & Vp/Va Copolymer | 13.000 |
|  | GRANSIL GCM-5 | Cyclopentasiloxane & Polysilicone-11 | 11.000 |
| D | GRANSIL EP-9 | Polysilicone-11 & Water & Laureth-12 & Phenoxyethanol & Ethylhexylglycerin | 10.000 |
| E | GRANSIL 530 | Dimethicone | 2.000 |
|  | PHYTOLANE LS | Olive Squalane | 2.000 |
|  | OLEIC ACID | Oleic Acid | 0.500 |
|  | DIMETHICONE, 20 CST | Dimethicone | 2.000 |

-continued

| Phase | Ingredient | INCI | % |
|---|---|---|---|
| F | KOH, 10% AQ SOL. | Water & Potassium Hydroxide | 2.000 |
| G | HYDROLITE-5 | Pentylene Glycol | 3.000 |
| H | SIMULGEL EG | Sodium Acrylate/Sodium Acryloyldimethyl Taurate Copolymer & Isohexadecane & Polysorbate 80 | 0.500 |
| I | ARGIRELINE ® NP | Acetyl Hexapeptide-8 | 5.000 |
|   | MAGNOLIA SUPER EXTRACT | Magnolia Grandiflora Bark Extract | 0.100 |
| J | XEP-018* | WATER & MU-CONOTOXIN Cniiic | 5.000 |
|   | X-50, 0.10% AQ. SOL. | Lactic Acid/Glycolic Acid Copolymer & Polyvinyl Alcohol & Dextran & Pamitoyl-Heptapeptide & Pantothenic Acid-Heptapeptide-Cu | 1.000 |
| K | CL-2080 | Polyethylene | 5.000 |
|   | TIMIRON SUPER RED | Mica & Ci 77891 | 2.000 |
| L | RED NO. 4 IN BUTYLENE GLYCOL, SOL. 1% | Butylene Glycol & Red No. 4 | 0.040 |
| M | Fragrance |  | 0.350 |
|   |   | Total: | 100.000 |

Procedure:
1. Weigh Phase A in the main kettle equipped with homogenizer. Sprinkle in Carbopol Ultrez 10 Polymer with mixing. Then, heat to 75-80 C.
2. Cool Phase A to 50 C with mixing.
3. Add Phase B. Mix until homogeneous.
4. Add Phase C, Phase D and Phase E consecutively, mixing well between each.
5. Add Phase F and Phase G consecutively, mix well between each.
6. Add Phase H and mix well.
7. Add each ingredient of Phase I and Phase J individually. Mix well between each.
8. Add Phase K and mix well.
9. Add Phase L and mix until homogeneous.
10. Add Phase M. Mix until uniform.
11. Check pH. Adjust to pH 7.

Example 2

A study was performed to evaluate the performance of the anti-aging test product of Example 1, except that XEP-018 was replaced with XEP-3 0. The product was tested over a 4-week period. A minimum of thirty healthy female subjects between the ages of 35 and 65 were inducted into this study. Subjects used the product daily as follows:

"Apply twice daily to clean dry skin as the first step in your usual skin care routine. Pump a small amount (2 to 3 pumps (about 0.5 g to about 1.0 g)) onto your fingertips blending a thin layer over the entire face and under eye area. Wait a few seconds before applying additional products. In the AM, follow with your daytime moisturizer and foundation if desired. Before bed, repeat application followed by your night cream. May be applied to the throat and neck if desired."

The following methods were used to observe improvements in skin texture and wrinkles, elasticity, hydration, and skin brightness. No unexpected adverse reactions were observed in any of the subjects.

Surface Evaluation of Living Skin Via Visioscan

The Visioscan (Courage and Khazaka) takes a direct image of living skin using a measuring head containing a CCD-camera and two metal halogen lamps positioned opposite each other in order to ensure even illumination of the measuring field on the skin. The grey level distribution of the pixels in the image corresponds to different phenomena (white pixels represent desquamation on skin, dark pixels represent lines and wrinkles). The software with the Visioscan automatically calculates skin roughness parameter. (See e.g., Fischer, T. W., et al., Direct and non-direct measurement techniques for analysis of skin surface topography, Skin Pharmacol. Appl. Skin Physiol., 12:1-11 (1999); Farwick, M., et al., An EC-derived Tetrapeptide to Counter balance ECM Degeneration, Cosmetic & Toiletries Magazine, 124(6) (Jun. 6, 2009).)

Skin Elasticity Via Cutometer

A Cutometer SEM 575 (Courage+Khazaka) was used to measure skin viscoelastic properties. The measuring principle is based on a suction method. Negative pressure is created in the device, which can be regulated between 20 and 500 mbar. Skin is drawn into a calibrated aperture of the probe by negative pressure where skin penetration depth is determined by a non-contact optical measuring system. The optical measuring system consists of a light transmitter and a light recipient, as well as two glass prisms facing each other, which project the light from transmitter to recipient. The light intensity will vary due to the penetration depth of the skin. (See e.g., Agache, P. G., et al., Mechanical properties and Young's modulus of human skin in vivo, Arch. Dermatol. Res., 269:221 (1980); de Rigal, J. and Leveque, J. J., In vivo measurement of the stratum corneum elasticity, Bioeng. Skin, 1:13 (1985)).

Skin Moisturization—Electroconductivity Via Novameter

A Nova Dermal Phase Meter, Model DPM 9003 (Nova, Technology Corp., Gloucester, Mass.) was used to obtain measurements of skin surface impedance to determine electroconductivity of the treatment sites. This meter provides a relative measure of the retained water content of the skin as a function of the skin's dielectric value. Skin impedance was recorded automatically when equilibrium was achieved. (See e.g., Leveque, J. J. and de Rigal, J., Impedance Methods for Studying Skin Moisturization, J. Soc. Cosmet. Chem., 34:419-428 (1983)).

Skin Color Brightness/Lightness Data [L*] Via Chromameter

The Minolta CR-200 Chromameter was used to detect subtle changes in color by a three dimensional profile of hue, value and chroma. These characteristics were then translated into color coordinates (a*, b* and L*) whose spacing was considered to correlate with the color changes perceived by the human eye. Any increase in the L* coordinate indicated lightening of the color. Any diminution of the L* coordinate indicated darkening of color.

The data reflects changes in skin color where test site (hyperpigmentation area) baseline readings are considered 0% and the lightest, clear skin (natural skin tone/color) for each panelist is considered 100%. As noted, clear skin is defined as the natural, untanned skin tone/color for each individual.

Visioscan, Cutometer, Novameter and Chromameter readings were obtained. These readings were totaled and average scores are reported. Data obtained is reported as percentage difference from baseline for each time point, where applicable.

Visioscan

Surface evaluation of living skin via Visioscan demonstrated decrease in (SEr) parameter associated with the depth of fine lines and wrinkles. The reductions were statistically significant at each evaluation time point.

| Roughness reduction [SEr] via Visioscan | | |
| --- | --- | --- |
| Study TimePoint: | Week 2 | Week 4 |
| % Difference: | −18.75%* | −31.67%* |
| Max % Improvement: | −37.39% | −55.84% |

*Statistically Significant

Cutometer:

Evaluation performed using Cutometer indicated increases in biological elasticity/flexibility on the test sites treated with the test product. The increases were statistically significant at Week 2 and Week 4 evaluation time points.

| Skin Elasticity (R7) via Cutometer | | | |
| --- | --- | --- | --- |
| Study Time Point: | 15 Minutes | Week 2 | Week 4 |
| % Difference: | 2.63% | 4.40%* | 7.07%* |
| Max % Improvement: | 24.52% | 25.20% | 27.46% |

*Statistically Significant

Novameter:

Novameter readings demonstrated that the test product increased skin moisture content. Increases in skin moisture content were statistically significant at 15 minutes after intial test product application and after 2 weeks of product use.

| Electroconductivity via Novameter | | | |
| --- | --- | --- | --- |
| Study Time Point: | 15 minutes | Week 2 | Week 4 |
| % Difference: | 5.68%* | 5.23%* | 2.12% |
| Max % Improvement: | 33.52% | 36.05% | 29.29% |

*Statistically Significant

Chromameter:

Treatment with the test product resulted in increased L* values associated with skin lightening. The increases were statistically significant at each evaluation time point.

| Skin Color Brightness/Lightness Data [L*] via Chromameter | | | |
| --- | --- | --- | --- |
| | 15 Minutes | Week 2 | Week 4 |
| % Difference: | 13.16%* | 17.49%* | 36.31%* |
| Max % Improvement: | 50.17% | 56.70% | 59.48% |

*Statistically Significant

Example 3

A study was performed to evaluate the performance of the anti-aging test product of Example 2 over a 14 day period. A minimum of twelve healthy female subjects between the ages of 35 and 65 were inducted into this study.

The product was applied as follows:

"Apply twice daily to clean, dry skin as the first step in your usual skin care routine. Pump a small amount (2 to 3 pumps (about 0.5 g to about 1.0 g)) onto your fingertips blending a thin layer over the entire face and under eye area. Wait a few seconds before applying additional products. In the AM, follow with your daytime moisturizer and foundation if desired. Before bed, repeat application followed by your night cream. May be applied to the throat and neck if desired."

The following non-invasive methods were used to evaluate results:

Detailed, high resolution before and after product application digital photographs were taken, with fixed camera background, distances, angles, settings, lighting, panelist positioning, color bars, white balance, standardized and digitally certified un-retouched. Each stage in the progression of treatment was photographically documented. These photographs provide a visual record for claim substantiation. The photographs of each woman's face are placed side-by-side so as to compare the appropriate designated test areas as well as general locations on the face (Matched Scientific Photographs). These photographs provide a visual record of the efficacy of the product on the subject's face.

The Matched Scientific Photographs were evaluated using PhotoGrammetrix™ Image Analysis, which allows capturing and quantification of skin conditions. PhotoGrammetrix™ Image Analysis readings were collected at baseline and day 14, after twice daily use of the test product.

Statistically significant data obtained through Photo-Grammetrix™ Image Analysis of the Matched Scientific Photographs demonstrated that The average of wrinkle reduction across the sample was 64%.

83% of the sample had wrinkle reduction of 38% or better.

42% of the sample had wrinkle reduction of 70% or better.

The top quartile had wrinkle reduction of 90% or better.

At the maximum end of the range, one participant's wrinkles were reduced by 99%.

| N-9289A | Day 14 |
| --- | --- |
| Average % Reduction | 64.19% * |
| Maximum % Reduction | 99.09% |

The above description is provided for the purpose of teaching the person of ordinary skill in the art how to practice the present invention, and it is not intended to detail all those obvious modifications and variations which will be apparent to the skilled worker upon reading the description. It is intended that all such obvious modifications and variations be included within the scope of the present invention, which is defined by the following claims. The claims are intended to cover the claimed components and steps in any sequence which is effective to meet the objectives there intended, unless the context specifically indicates the contrary.

What is claimed is:

1. A formulation for topical administration to the skin comprising dimethyl isosorbide, oleic acid, and a first mixture of water, dimethylacrylamide/acrylic acid/polystyrene ethyl methacrylate copolymer, *Oryza sativa* (rice) bran extract, phenoxyethanol, and sodium benzoate, wherein the formulation comprises about 1-20% dimethyl isosorbide, about 0.1-20% oleic acid, and about 0.5-10% of the first mixture of water, dimethylacrylamide/acrylic acid/polystyrene ethyl methacrylate copolymer, *Oryza sativa* (rice) bran extract, phenoxyethanol, and sodium benzoate.

2. The formulation of claim 1, comprising about 6% dimethyl isosorbide, about 0.5% oleic acid, and about 1.5% of the first mixture of water, dimethylacrylamide/acrylic acid/polystyrene ethyl methacrylate copolymer, *Oryza sativa* (rice) bran extract, phenoxyethanol, and sodium benzoate.

3. The formulation of claim 1, further comprising one or more active agents, wherein said one or more active agents comprises a second mixture of water, *Boswellia* serrate resin extract, *Centella asiatica* extract, phenoxyethanol, and sodium benzoate.

4. The formulation of claim 1, comprising about 1-20% dimethyl isosorbide, about 0.1-1% oleic acid, about 0.5-4% of the first mixture of water, dimethylacrylamide/acrylic acid/polystyrene ethyl methacrylate copolymer, *Oryza sativa* (rice) bran extract, phenoxyethanol, and sodium benzoate, and further comprising about 0.5-5% of a second mixture of water, *Boswellia* serrate resin extract, *Centella asiatica* extract, phenoxyethanol, and sodium benzoate.

5. A method for improved delivery of an active agent to skin, said method comprising administering a formulation that comprises about 1-20% dimethyl isosorbide, about 0.1-20% oleic acid, and about 0.5-10% of a first mixture of water, dimethylacrylamide/acrylic acid/polystyrene ethyl methacrylate copolymer, *Oryza sativa* (rice) bran extract, phenoxyethanol, and sodium benzoate.

6. The method of claim 5, wherein said formulation further comprises one or more active agent, wherein said one or more active agent comprises a second mixture of water, *Boswellia* serrate resin extract, *Centella asiatica* extract, phenoxyethanol, and sodium benzoate.

7. The method of claim 5, wherein the dimethyl isosorbide and the oleic acid open skin pores, facilitating absorption of one or more active agents for moisturizing skin.

8. The method of claim 5, wherein the first mixture of water, dimethylacrylamide/acrylic acid/polystyrene ethyl methacrylate copolymer, *Oryza sativa* (rice) bran extract, phenoxyethanol, and sodium benzoate closes skin pores, facilitating retention of one or more active agents for moisturizing skin.

9. The method of claim 5, wherein said formulation comprises about 1-20% dimethyl isosorbide, about 0.1-1% oleic acid, about 0.5-4% of the first mixture of water, dimethylacrylamide/acrylic acid/polystyrene ethyl methacrylate copolymer, *Oryza sativa* (rice) bran extract, phenoxyethanol, and sodium benzoate, and further comprises about 0.5-5% of a second mixture of water, *Boswellia* serrate resin extract, *Centella asiatica* extract, phenoxyethanol, and sodium benzoate.

10. A method of making a formulation for topical administration to the skin, said method comprising combining about 1-20% dimethyl isosorbide, about 0.1-20% oleic acid, and about 0.5-10% of a first mixture of water, dimethylacrylamide/acrylic acid/polystyrene ethyl methacrylate copolymer, *Oryza sativa* (rice) bran extract, phenoxyethanol, and sodium benzoate.

11. The method of claim 10, further comprising combining one or more active agents, wherein said one or more active agents further comprises a second mixture of water, *Boswellia* serrate resin extract, *Centella asiatica* extract, phenoxyethanol, and sodium benzoate.

12. The method of claim 10, comprising combining about 1-20% dimethyl isosorbide, about 0.1-1% oleic acid, about 0.5-4% of the first mixture of water, dimethylacrylamide/acrylic acid/polystyrene ethyl methacrylate copolymer, *Oryza sativa* (rice) bran extract, phenoxyethanol, and sodium benzoate, and about 0.5-5% of a second mixture of water, *Boswellia* serrate resin extract, *Centella asiatica* extract, phenoxyethanol, and sodium benzoate.

* * * * *